(12) United States Patent
Smith (10) Patent No.: US 9,188,520 B1
(45) Date of Patent: Nov. 17, 2015

(54) TENSILE TESTING APPARATUS

(71) Applicant: Gregory Earl Smith, Lebanon, OH (US)

(72) Inventor: Gregory Earl Smith, Lebanon, OH (US)

(73) Assignee: ENGINEERED MINE SOLUTIONS, LLC, Lebanon, OH (US)

( * ) Notice: Subject to any disclaimer, the term of this patent is extended or adjusted under 35 U.S.C. 154(b) by 237 days.

(21) Appl. No.: 14/086,824

(22) Filed: Nov. 21, 2013

(51) Int. Cl.
*G01N 3/08* (2006.01)
*G01N 3/20* (2006.01)
*G01N 3/10* (2006.01)
*H04N 5/76* (2006.01)

(52) U.S. Cl.
CPC ... *G01N 3/10* (2013.01); *H04N 5/76* (2013.01)

(58) Field of Classification Search
CPC .................................. G01N 3/08; G01N 3/02
USPC ............................................................ 73/826
See application file for complete search history.

(56) References Cited

U.S. PATENT DOCUMENTS

| | | | |
|---|---|---|---|
| 3,721,119 A | 3/1973 | Strimel | |
| 3,776,030 A | 12/1973 | Strimel | |
| 3,835,699 A | 9/1974 | Strimel | |
| 3,943,819 A | 3/1976 | Charron | |
| 4,062,229 A | 12/1977 | Godfrey et al. | |
| 4,281,547 A | 8/1981 | Hinshaw et al. | |
| 4,318,302 A | 3/1982 | Choi | |
| 4,601,207 A | 7/1986 | Steblay | |
| 4,624,144 A | 11/1986 | Strimel | |
| 4,944,188 A | 7/1990 | Dial | |
| 5,232,311 A * | 8/1993 | Stankus | E21D 21/008 405/259.4 |
| 5,542,788 A * | 8/1996 | Stankus | E21C 41/16 33/1 H |
| 5,598,738 A * | 2/1997 | Buescher, Jr. | F16B 31/025 73/761 |
| RE36,019 E | 12/1998 | Stankus | |
| 6,041,660 A * | 3/2000 | Fujitaka | G01L 5/0033 73/826 |
| 6,370,962 B1 * | 4/2002 | Sullivan | G01N 3/08 73/826 |
| 7,324,007 B2 | 1/2008 | Sunderman et al. | |
| 8,224,631 B2 * | 7/2012 | Stankus | E21C 41/16 405/259.1 |

* cited by examiner

*Primary Examiner* — Lisa Caputo
*Assistant Examiner* — Jamel Williams (57) ABSTRACT

A tensile-testing apparatus (10) comprises a platen (40) for situating a tendon-type support system in manner mimicking its expected installation condition. A force-imposing device (20) imposes installation-expected forces and sensors (61, 71) sense displacement in the force-imposing direction. A station (80) collects force and displacement data and a station (90) outputs the collected data in format allowing system analysis.

20 Claims, 15 Drawing Sheets

TENSILE TESTING APPARATUS

BACKGROUND

A tendon type support system, such as a mechanical rock bolt system, can be used to stabilize rock in a tunnel or mine. Such a bolt system supports the rock that makes up the immediate roof structure by supporting it from a stronger or more stable rock structure that lies above.

SUMMARY

An apparatus is provided for tensile testing of a tendon-type support system that simultaneously tests the total system, subsystems, and individual components. Additionally or alternatively, the testing apparatus allows the system's tendon element to be anchored to a platen part in the same way as it is anchored in a field installation.

DESCRIPTION

Figure 1:
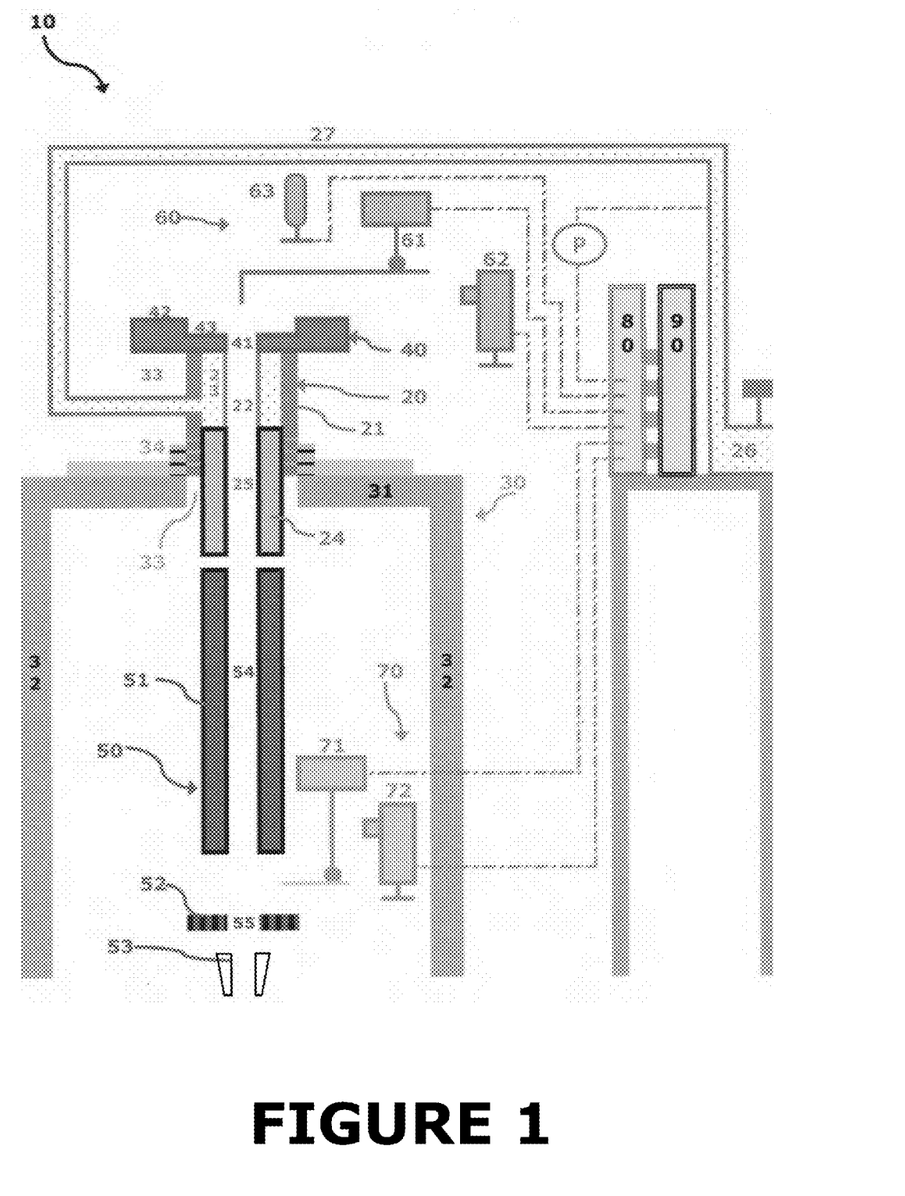
FIG. 1 shows an apparatus for tensile testing of a tendon-type support system.

Referring now to the drawings, and initially to FIG. 1, tensile testing apparatus 10 is shown. The apparatus 10 can be made more compact, light weight and portable than commercially available equipment whereby it can be easily broken down, transported by hand, and quickly reassembled to conduct tests at different locations as needed. The apparatus 10 can be constructed, for example, with a footprint of less than 10 square feet (e.g., about 3 feet by 3 feet) and/or with a weight less than 1000 pounds (e.g., around 500 pounds). Additionally or alternatively, the apparatus 10 can be adapted to test much longer specimens than conventional equipment and thus is useful in analyzing long specimens in their entirety.

The testing apparatus 10 comprises a force-imposing device 20 designed to impose force on the tendon-type support system in a manner duplicating that which it will encounter in its installation setting. The illustrated device 20 comprises a cylinder 21 having a central bore 22 and an annular fluid chamber 23 therearound. A ram 24 is slidably mounted within the chamber 23 so as to move vertically in response to fluid contained therein. The ram 24 has a central bore 25 aligned with the central bore 22 of the cylinder 21. A fluid source 26 (e.g., a pump) can be connected to the chamber 23 via hose 27 or other suitable conduit.

The cylinder-ram components of the force-imposing device 20 can be mounted on a table 30 having a horizontal platform 31 and vertical legs 32. The cylinder 21 extends partially through an opening 33 in the platform 31 and is held in place by a bracket 34.

The tensile testing apparatus 10 additionally comprises a platen 40 adapted to pose a tendon-type support system in a way representative of its installation setting. The platen 40 is fixed to the top of the cylinder 21 and has a central bore 41 aligned with those of the force-imposing device 20. An upper surface 42 surrounds the central bore 41 and includes a counterbore 43.

The tensile testing apparatus 10 further comprises an assembly 50 for fixturing the to-be-tested support system to the force-imposing device 20. In the illustrated apparatus 10, the fixturing assembly 50 includes a pipe 51, a washer 52, and locking elements 53. The pipe 51 has a central bore 54 and the washer 52 has a central opening 52 which are alignable with the ram's central bore 25.

Sensing equipment 60 can be situated to sense changes above the platen 40 and sensing equipment 70 can be situated to sense changes below the pipe 51 (or at least below the ram 24). This equipment can include electronic position sensors 61 and 71 linked to determine vertical displacement. Cameras 62 and 72 can be placed near the sensors 61 and 71 to visually record changes and video document a test from start to finish. A microphone 63 can also be strategically located to record relevant sounds associated with the testing. These sounds can include, for example, the "pops", "pings", "kings", "rings", and "booms" which occur as components deform, fail, and redistribute load to other components.

Figure 2:
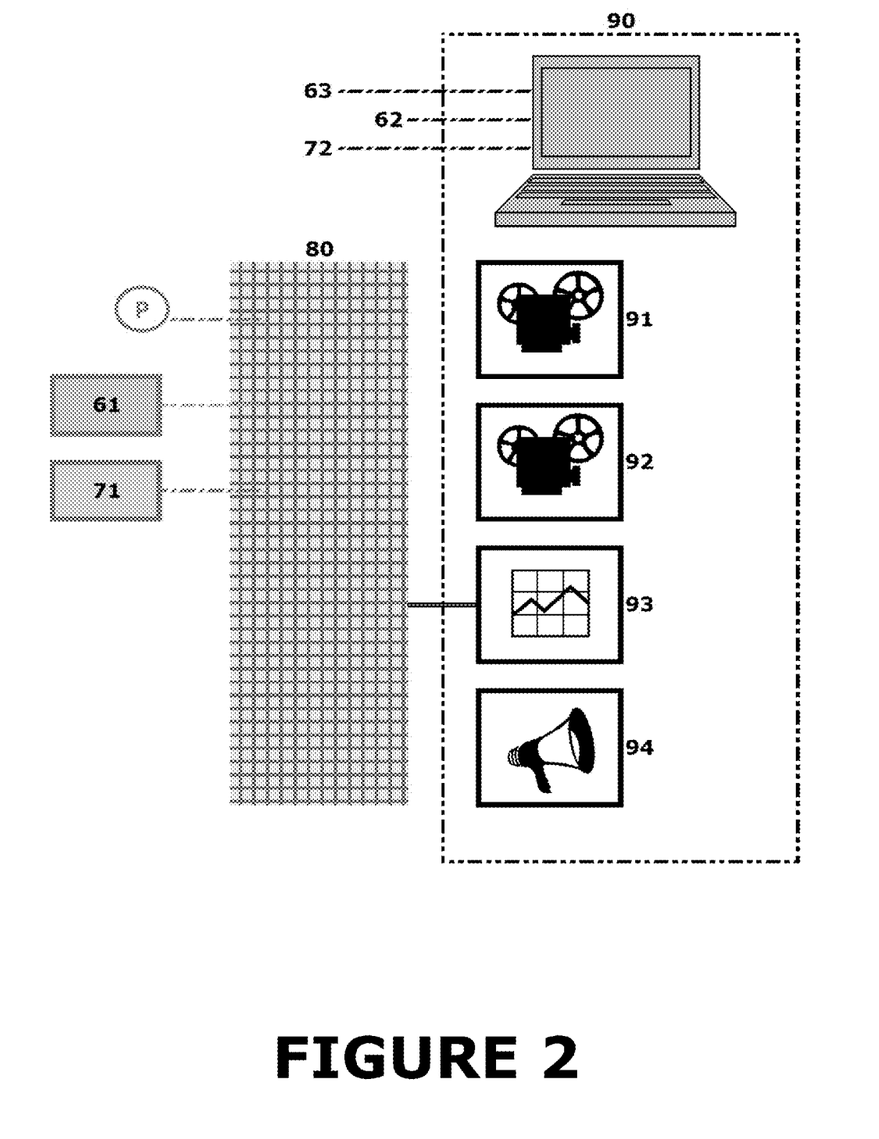
FIG. 2 shows output features of the apparatus.

A data-collecting station 80 can collect data from the force-imposing device 20 and the sensing equipment 60-70. As shown in FIG. 2, the data collecting station 80 can convey data to an output station 90 which outputs the data in visual formats 91-92, a graphical format 93, and/or graphical format 93. The output station 90 can be incorporated into a conventional laptop computer.

Figure 3:
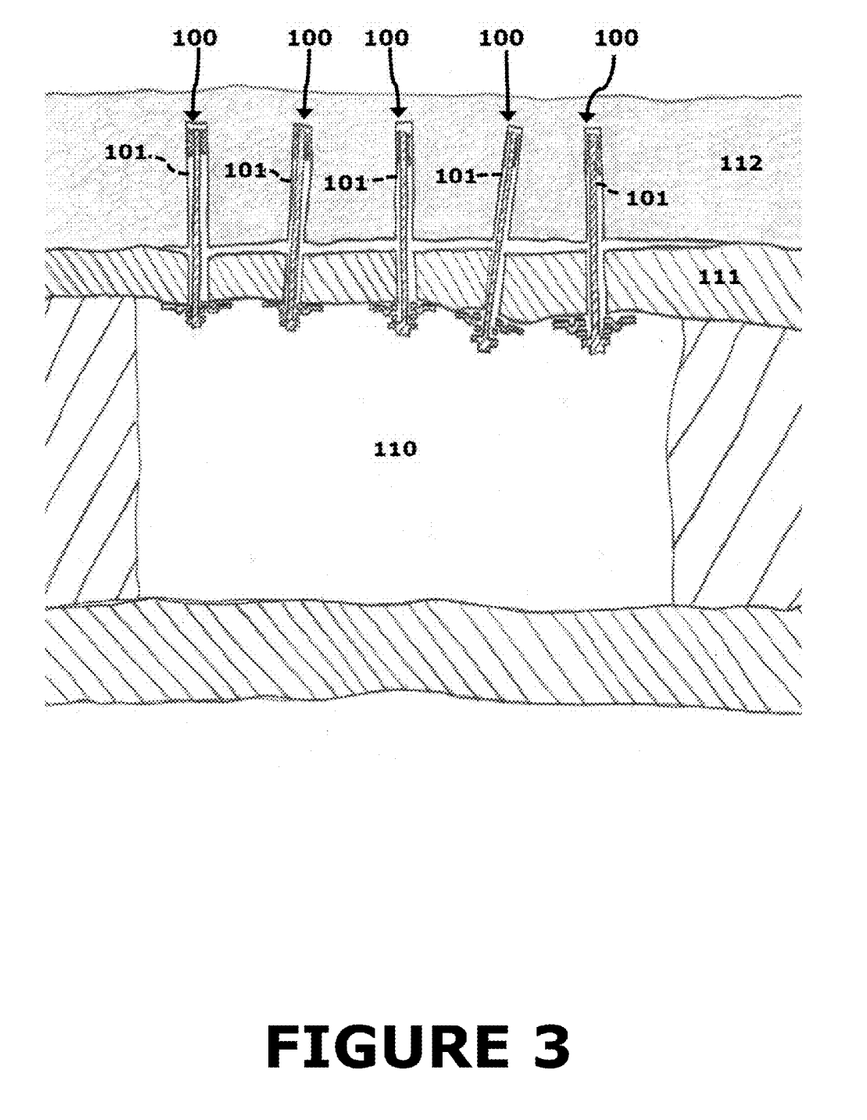
FIG. 3 shows tendon-type support systems in an installation condition.

The apparatus 10 can be used to tensile test a tendon-type support system, such as the mechanical rock bolt systems 100 depicted in FIG. 3. The illustrated support systems 100 are shown in a mine or tunnel 110. Each system 100 supports the rock that makes up the immediate roof structure 111 by supporting it from a stronger or more stable rock structure 112 that lies above.

The tendon-type support system 100 can involve a cylindrical borehole 101, drilled through the to-be-supported rock structure 111 and into the support-providing rock structure 112. As is best seen by referring to FIG. 4, the system 100 can comprise a roof bolt 120, an anchor 130, a roof plate 140, and a washer 150.

Figure 4:
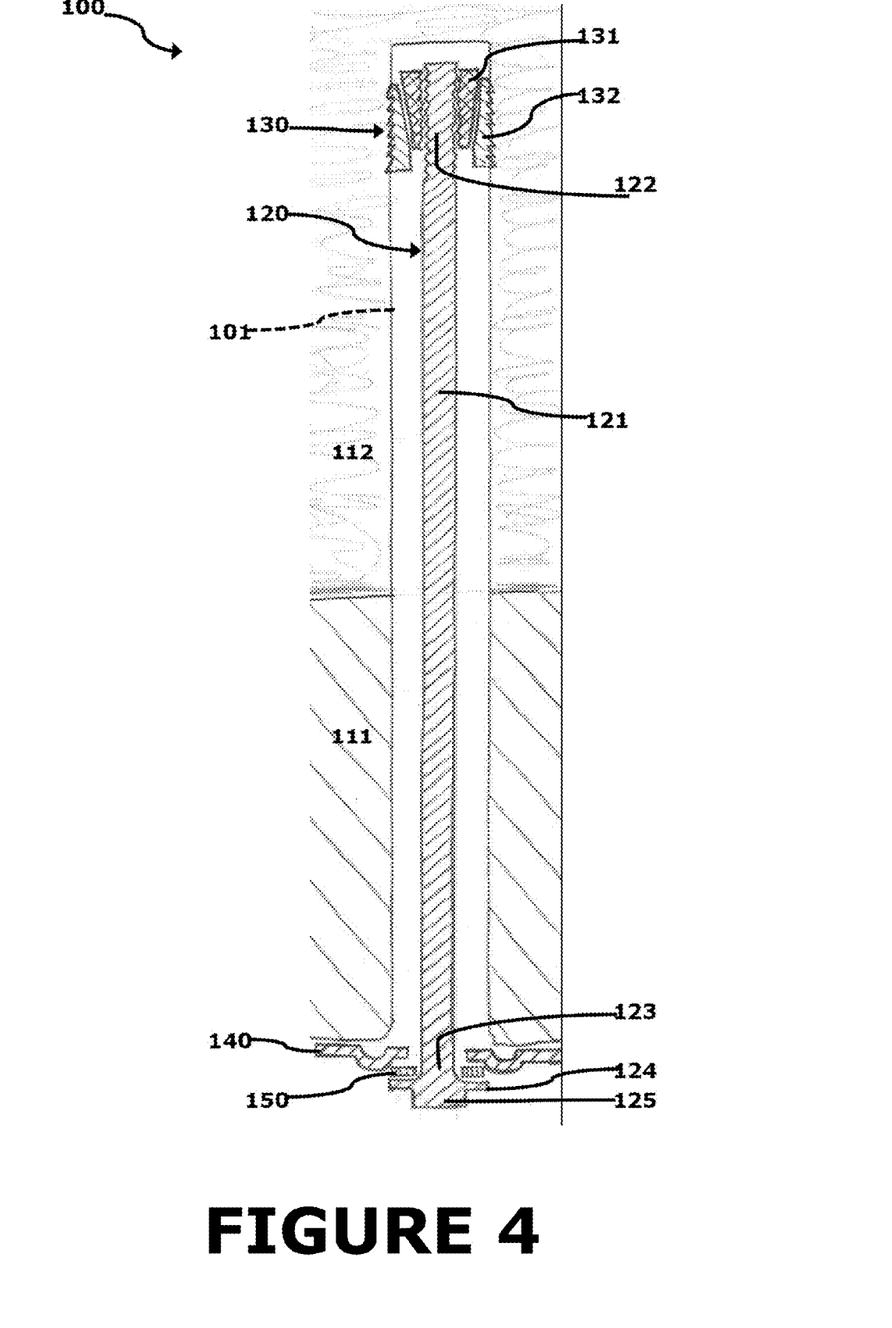
FIGS. 4-5 show a tendon-type support system before and after forces are imposed.

The rock bolt 120 constitutes the "tendon" element of the support system 100. It can comprise a cylindrical body 121 having an upper threaded portion 122 and a lower end 123. A circular flange 124 and a square bolt head 124 are located on the body's lower end 123. The anchor 130 is situated in an upper region of the borehole 101 and includes a wedge part 131 and a leaf part 132.

The upper threaded portion 122 of the bolt 120 is in contact with the anchor's wedge part 131. The wedge part 131 acts upon the leaf part 132 when the bolt 120 is pulled in a downward direction. The roof plate 140 has an upper face in contact with the roof rock structure 111 and a lower face adjacent an upper face of the washer 150.

Figure 5:
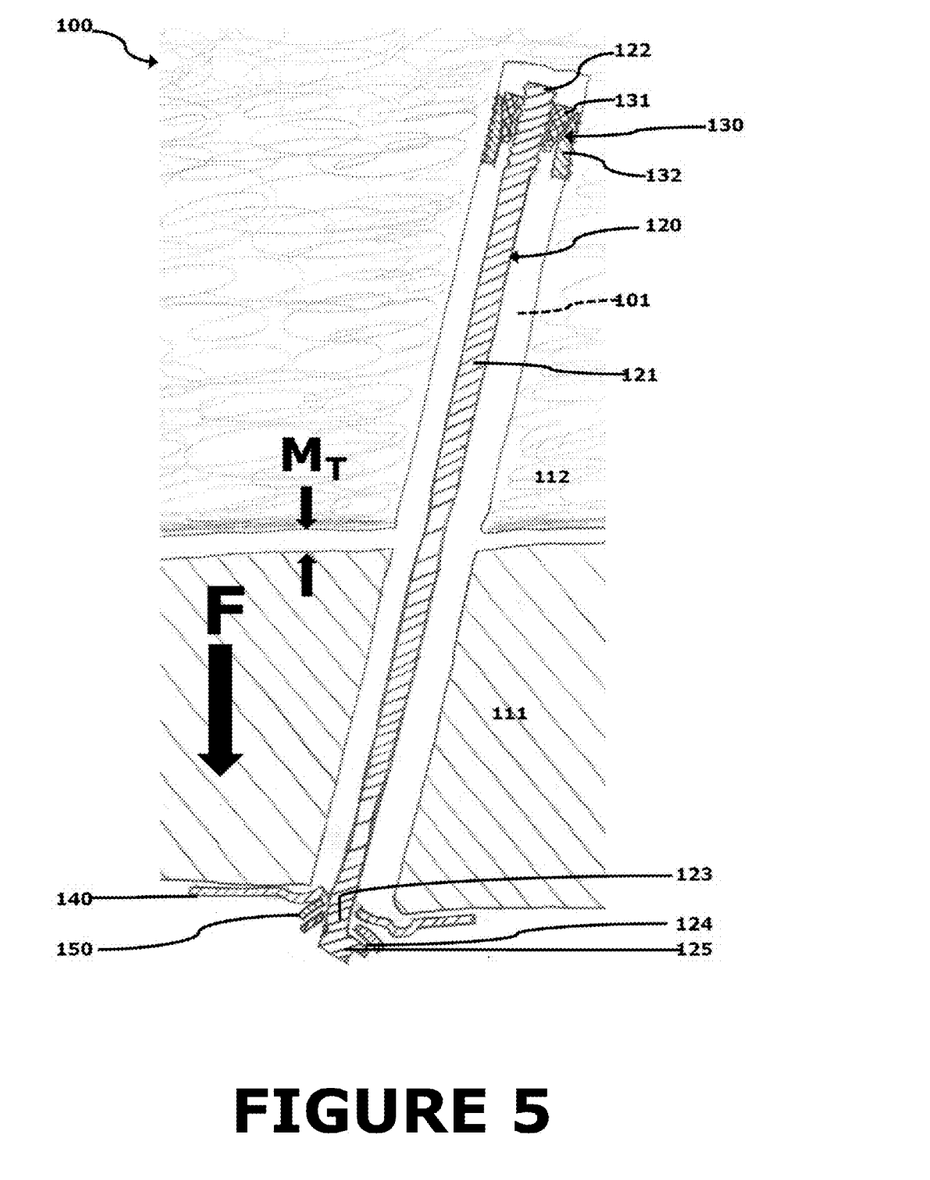

In FIG. 4, a tendon-type support system 100 is shown immediately after installation, prior to any force being applied. In FIG. 5, a system 100 is shown as it might exist after a typical Force F is applied. This Force F is transferred from the supported rock structure 111 to the bearing plate 140 to the washer 150, to the bolt flange 124 and then to the bolt head 125. From the bolt head 125, the Force F is transferred to the bolt body 121 to the threaded upper portion 122, into the anchor 130, and then into the stable rock structure 112.

In most installations, some or all of the components (i.e., the bolt 120, the anchor 130, the plate 140, and the washer 150) of the system 100 are deformed as a result of the Force F. And the rock structure 111 and the rock structure 112 will sometimes separate by a distance $M_T$.

Figure 6:
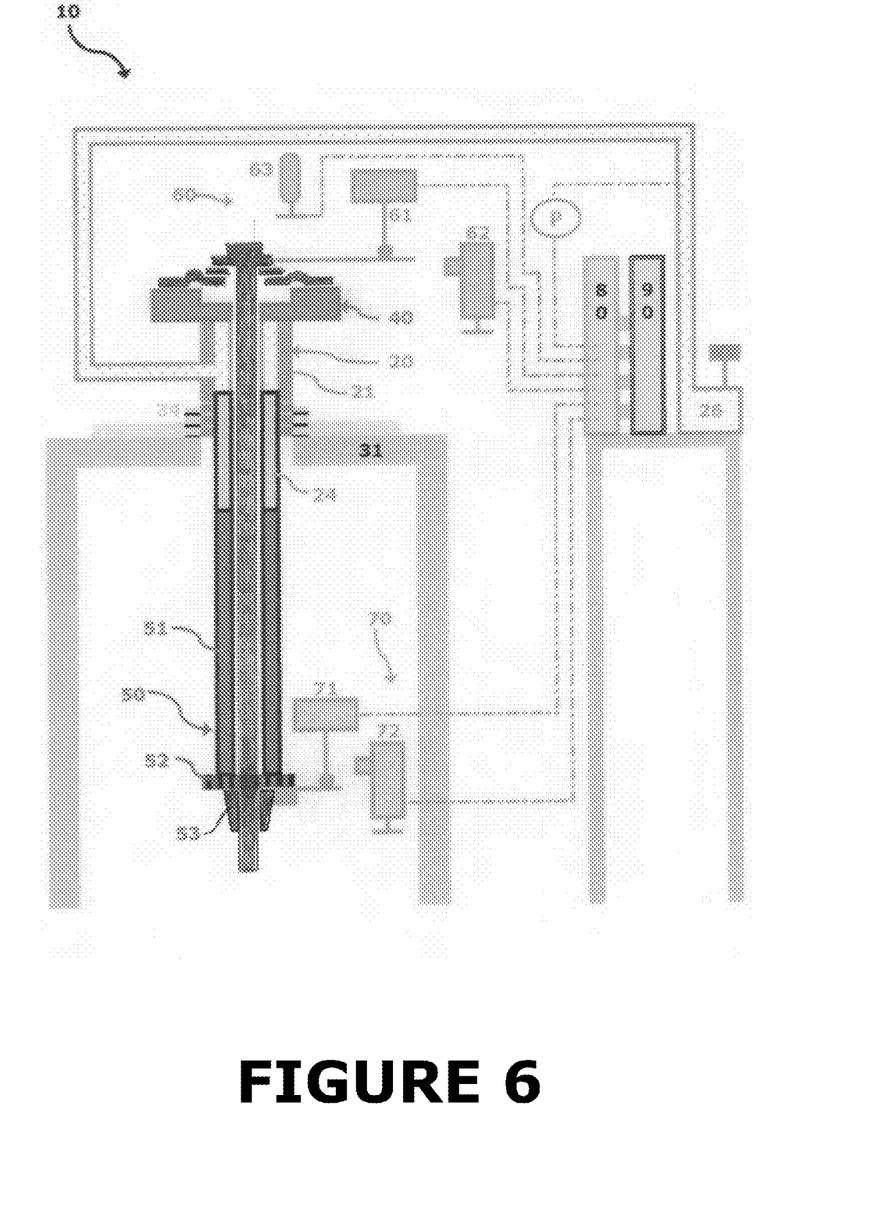
FIG. 6 shows the tendon-type support system mounted in the apparatus for testing.

To test the support system 100, it is mounted on the test apparatus 10 as shown in FIG. 6 in a manner resembling its installation, except up-side-down in orientation. Specifically, for example, the plate 140 and the washer 150 are placed on the platen 40. The bolt 120 is lowered through the aligned bores and through the fixturing pipe 51. The washer 52 and the wedge elements 53 are assembled onto the bolt's end portion 122 to secure it to the pipe 51.

Figure 7:
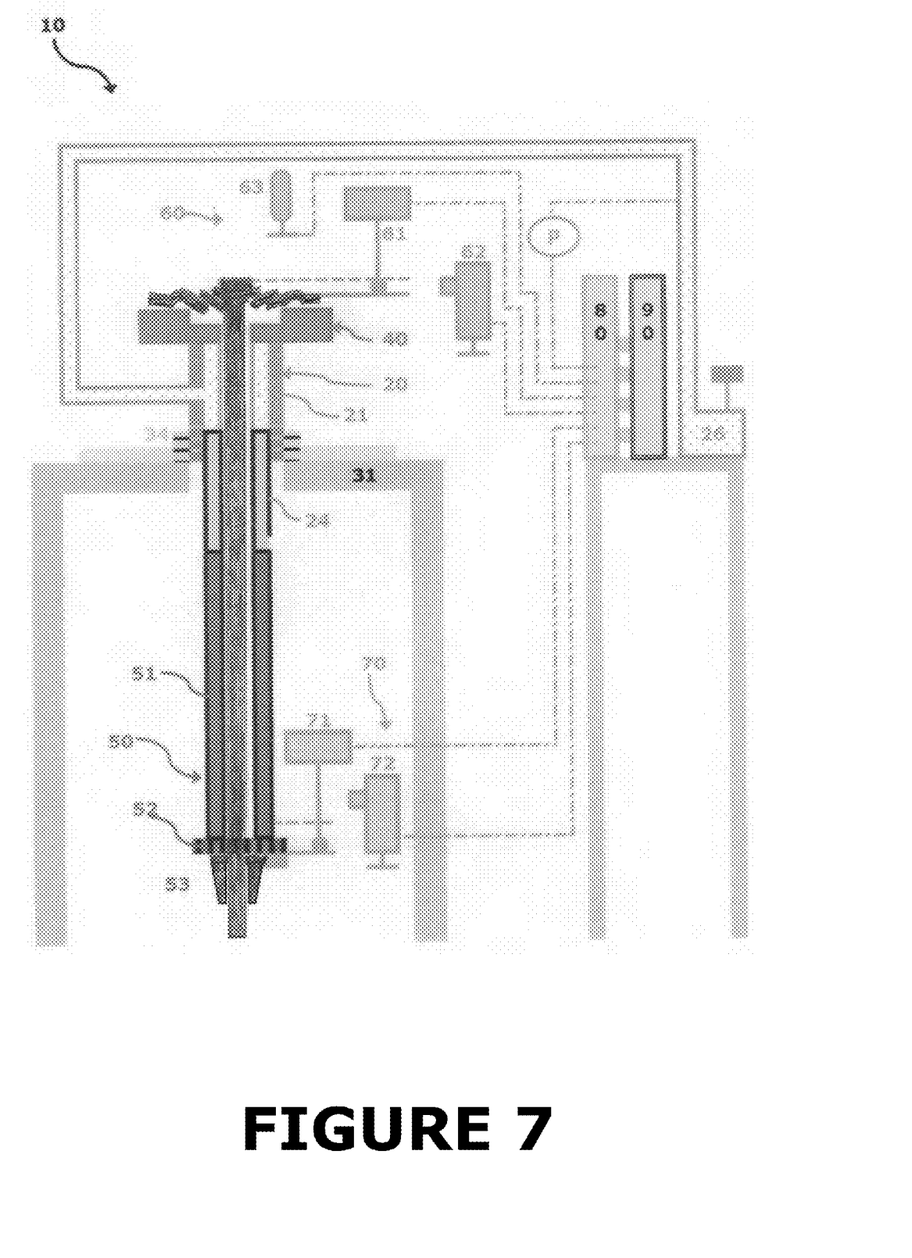
FIG. 7 shows the tendon-type support system being tested by the apparatus.
Figure 8A:
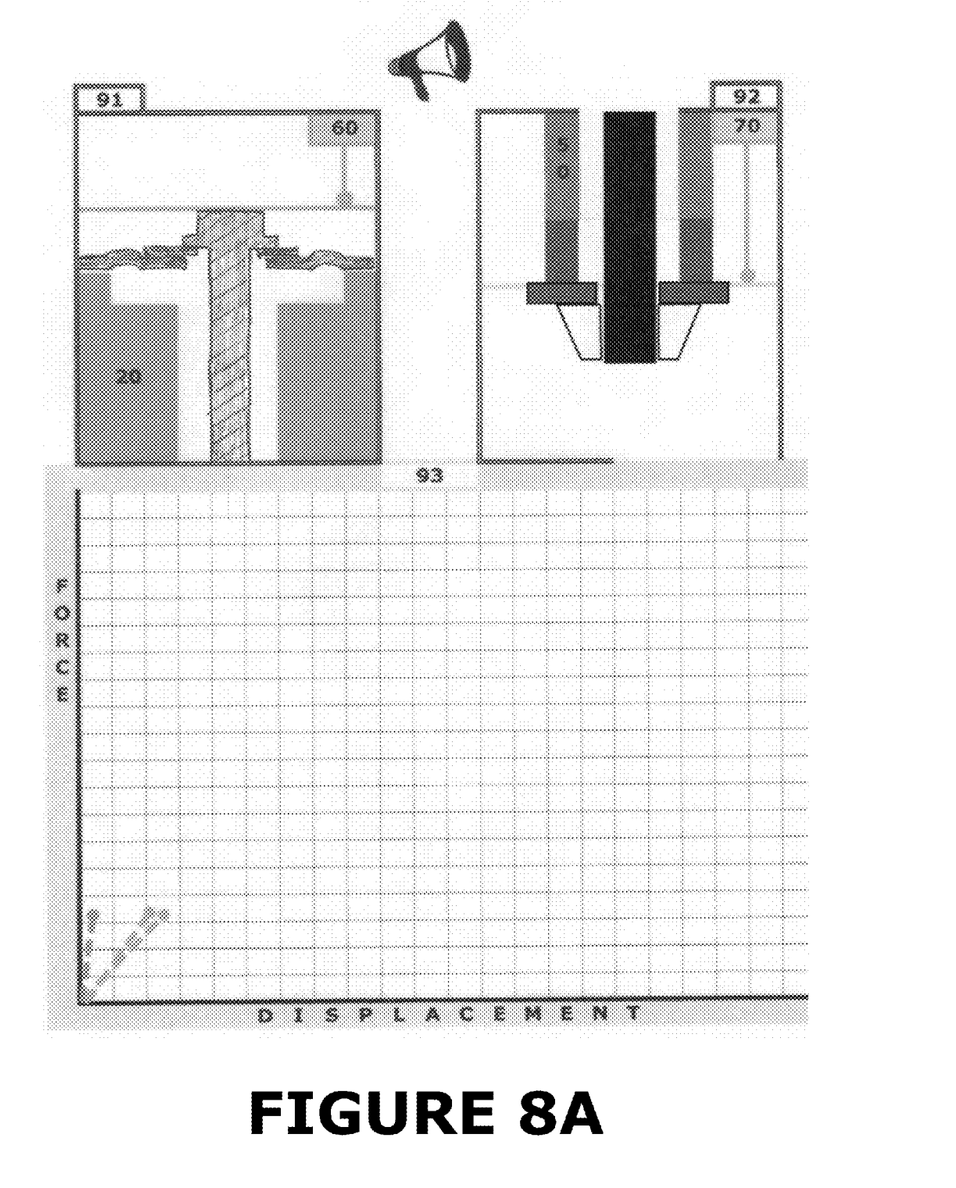
FIGS. 8A-8H show some comprehensive output formats that can be provided by the apparatus.
Figure 8B:
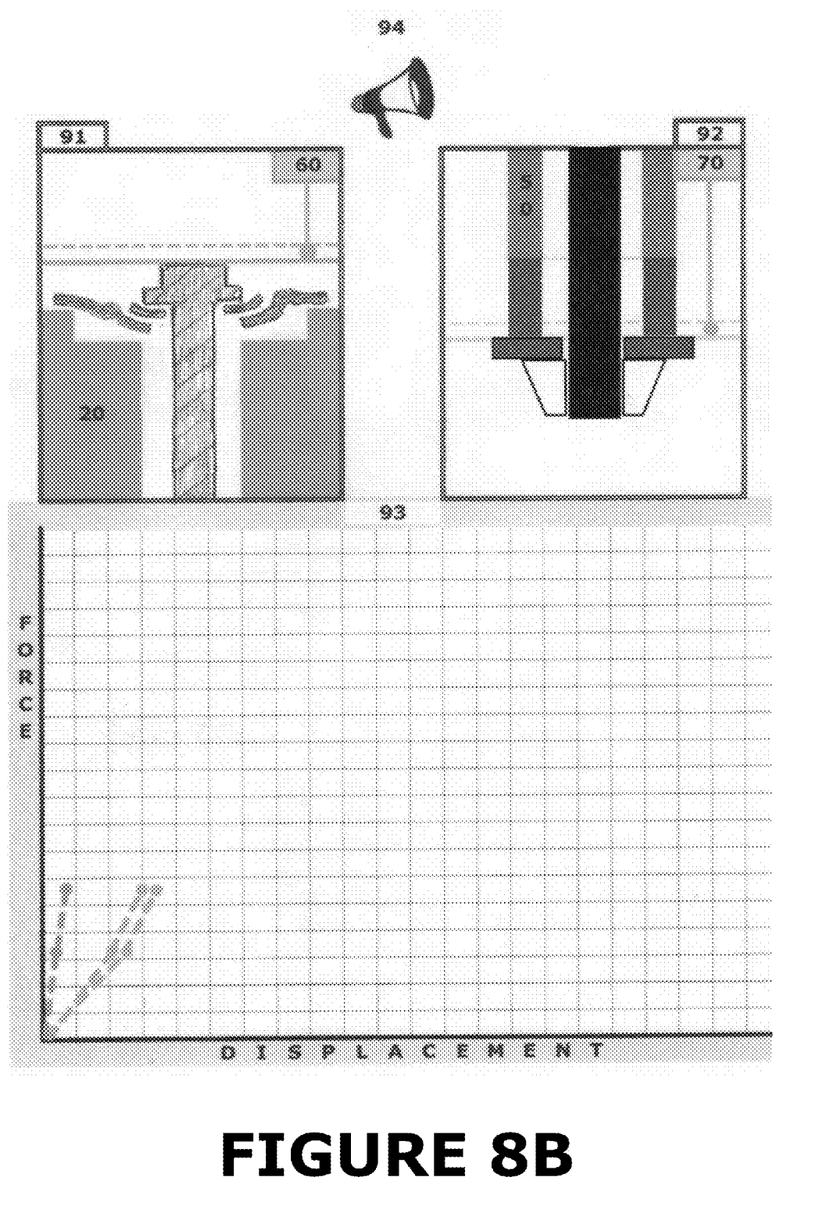
Figure 8C:
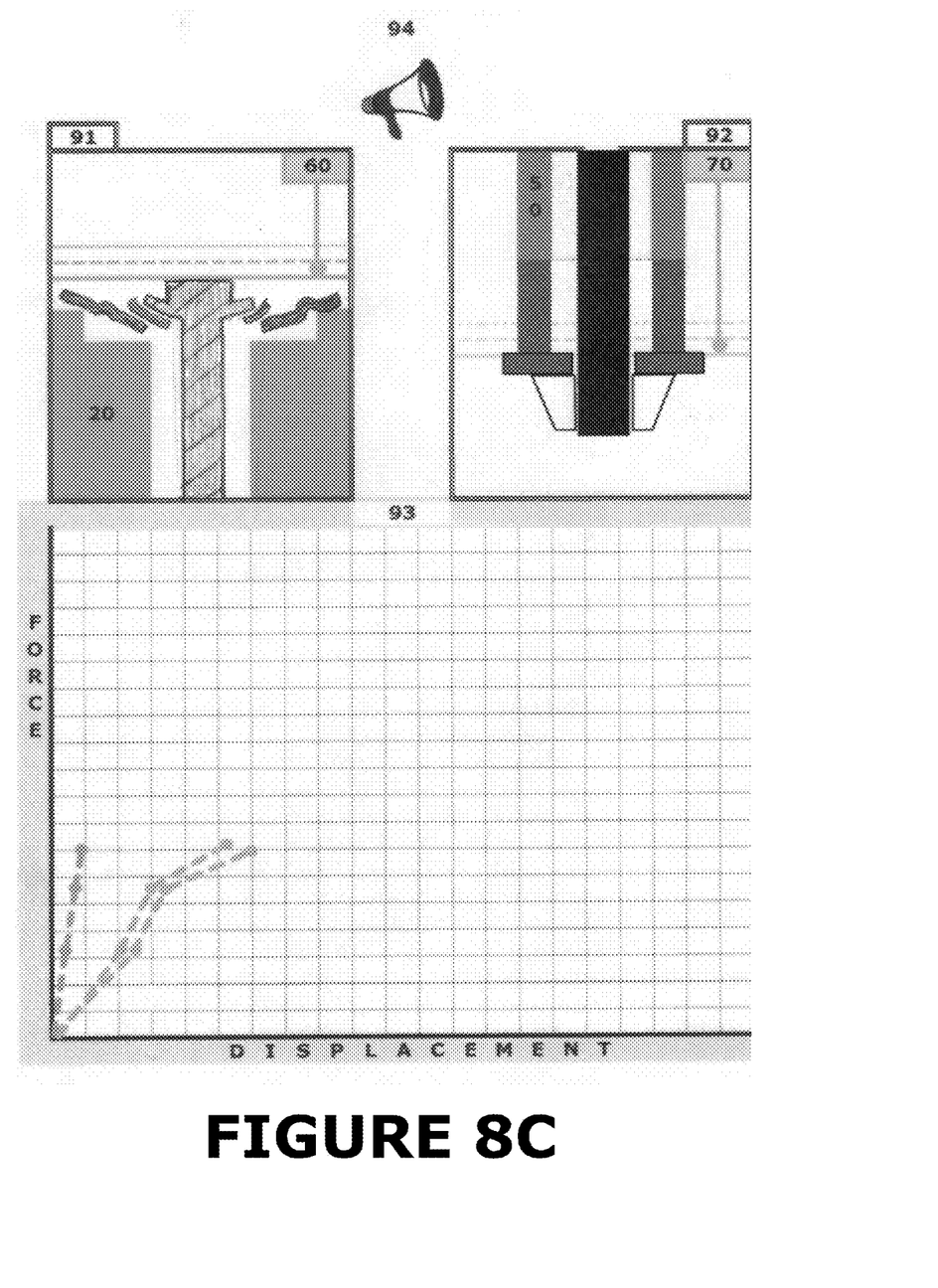
Figure 8D:
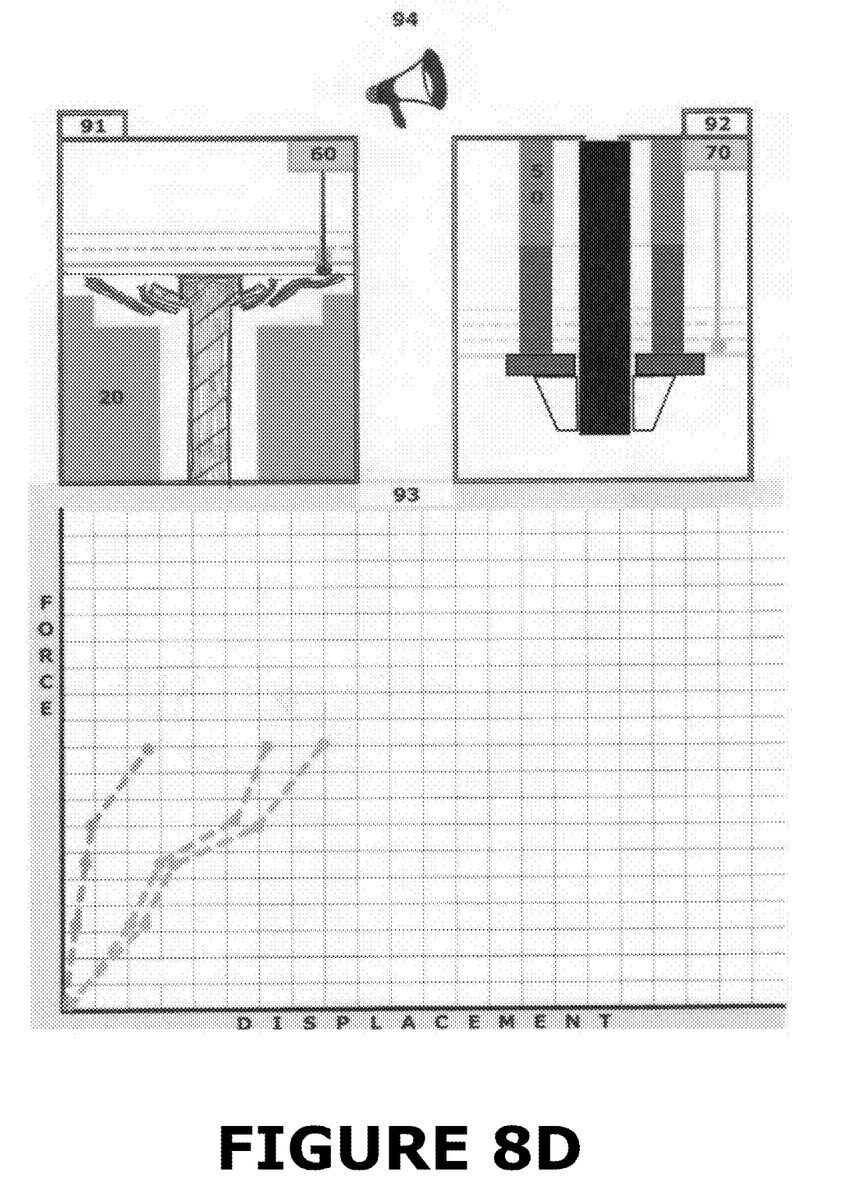
Figure 8E:
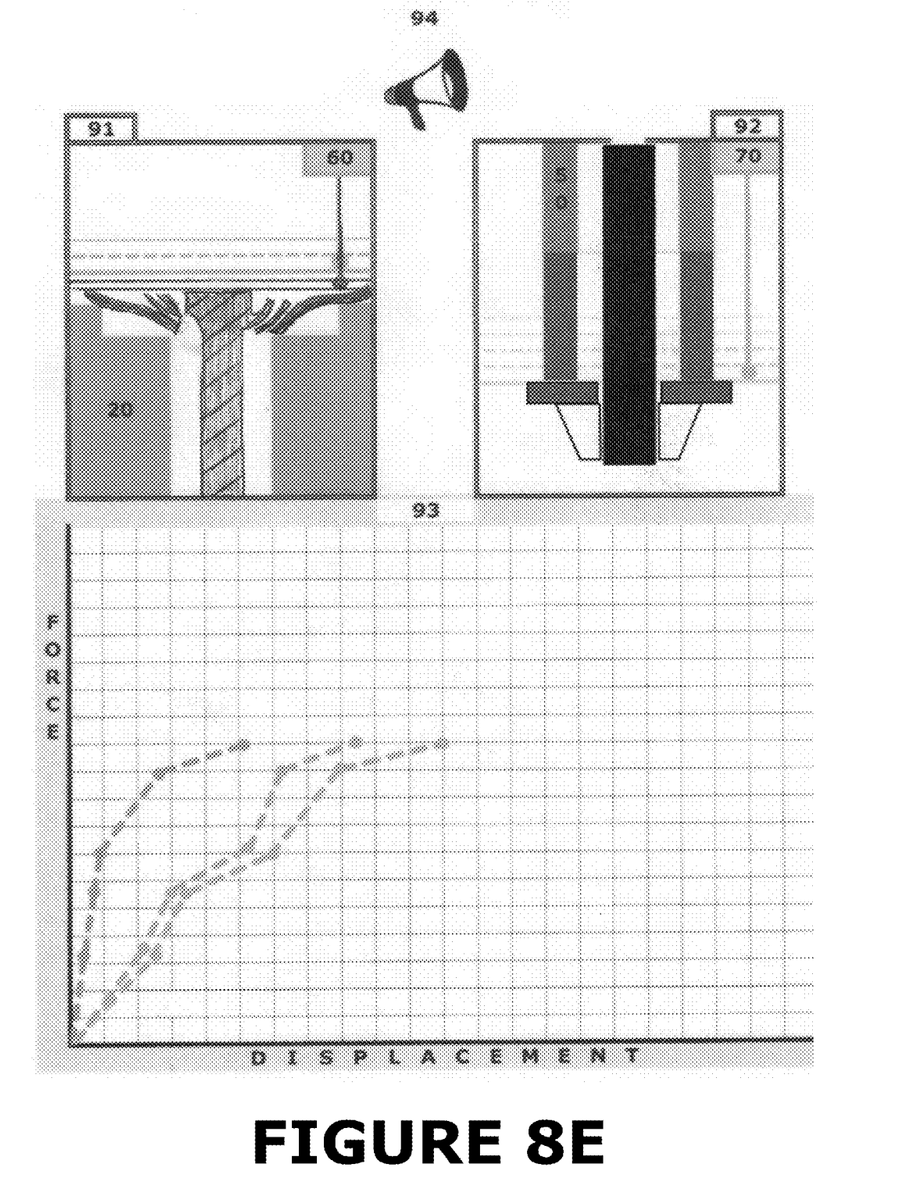
Figure 8F:
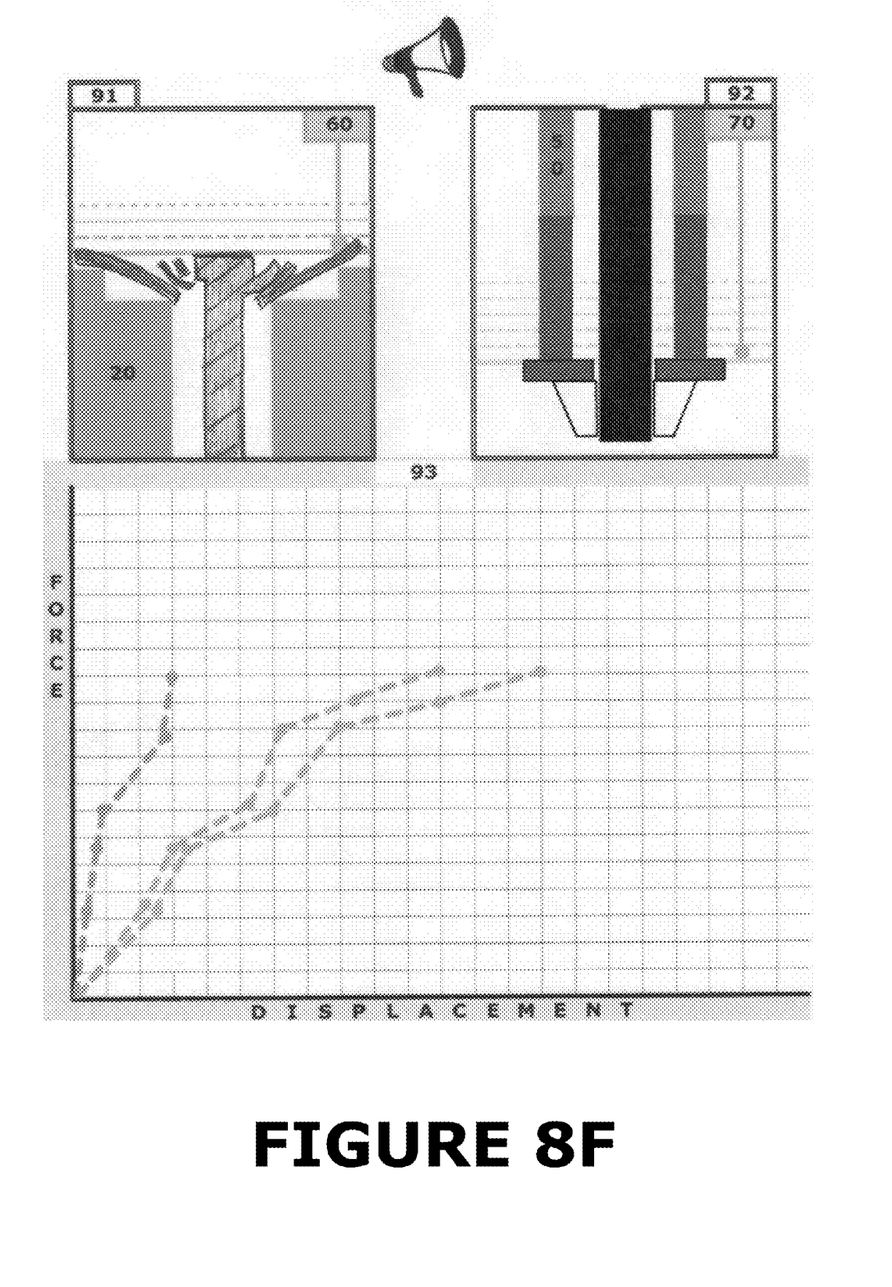
Figure 8G:
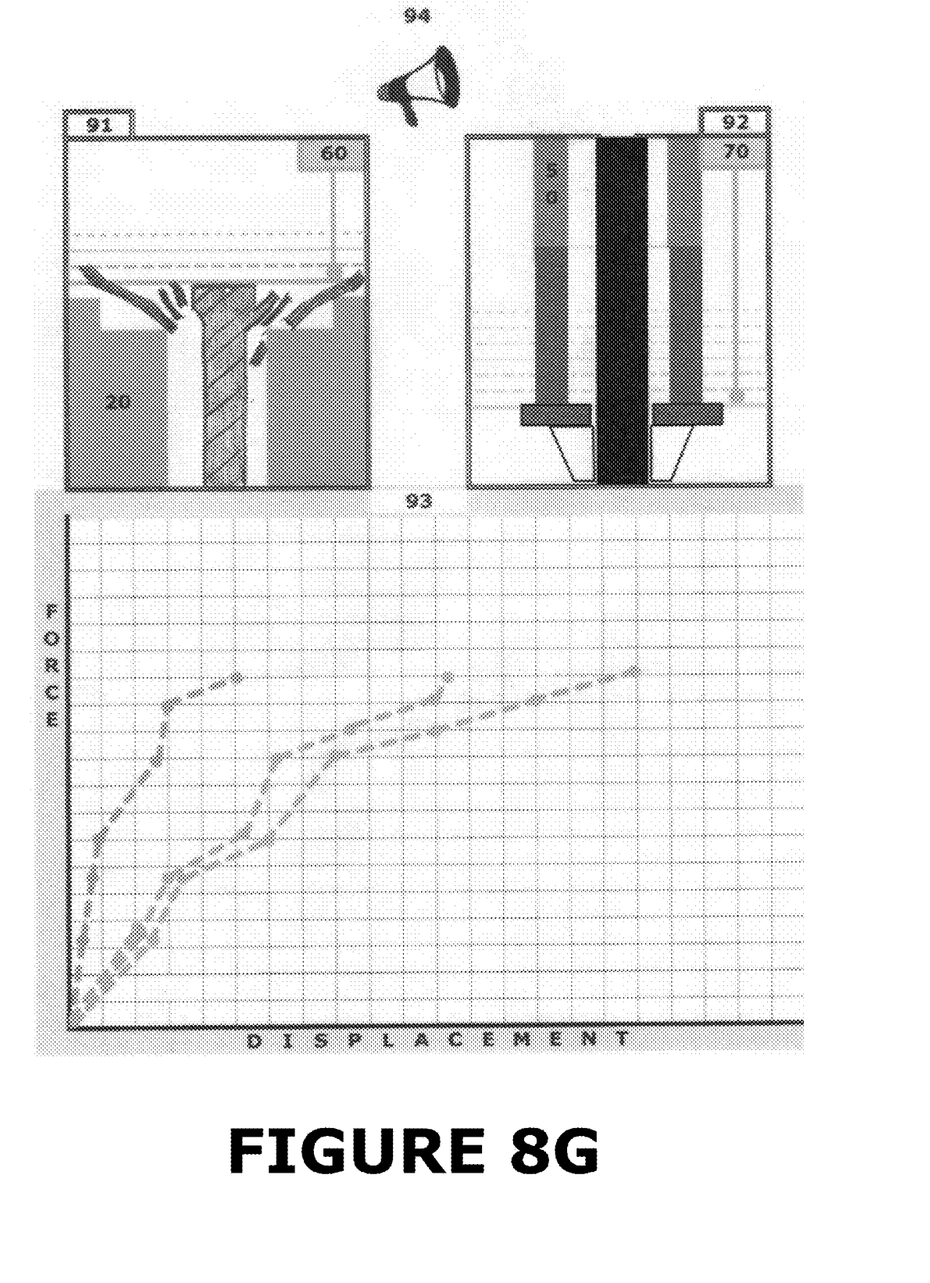
Figure 8H:
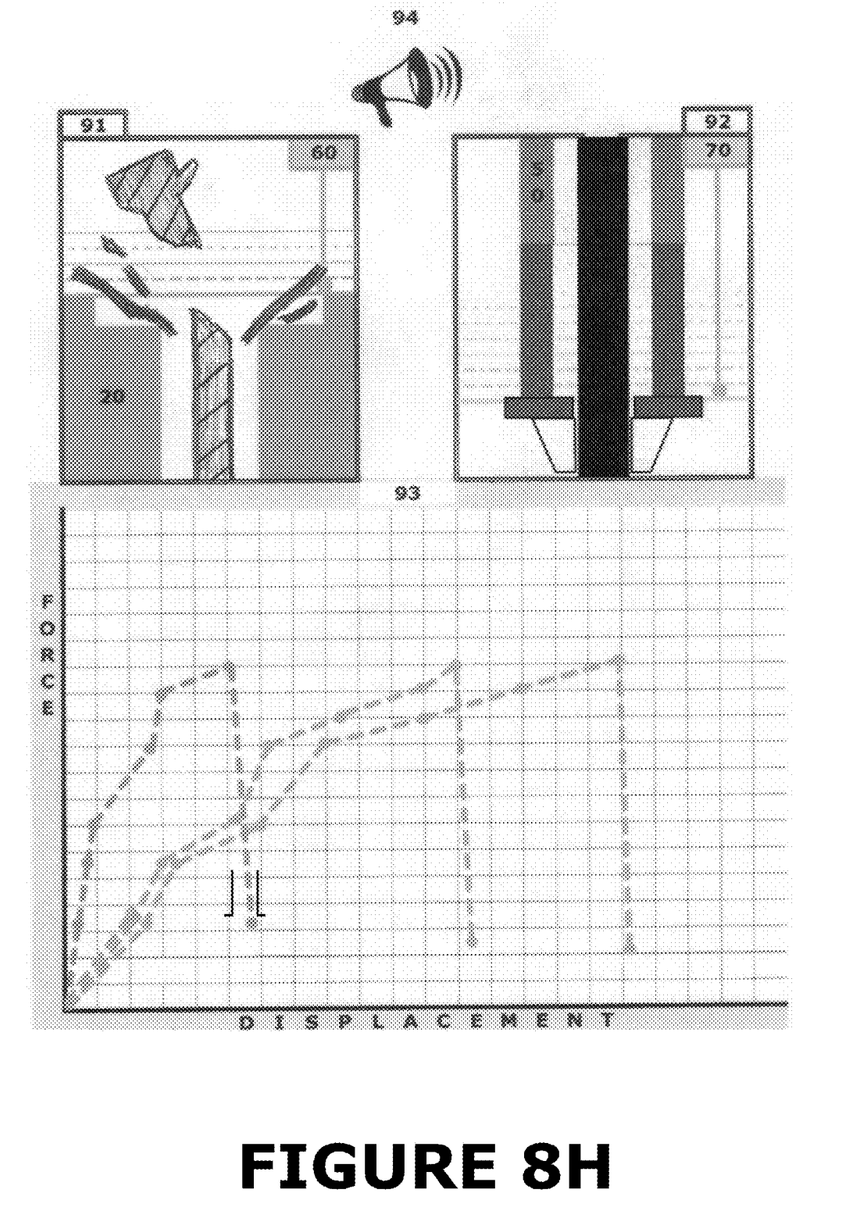

Once the support system 100 is mounted, fluid can be supplied (e.g., pumped) to the cylinder 21 from the source 26. This force simulates that experienced by the system 100 in its installation setting and thus it displaces in a corresponding manner. As force is applied, the sensor 61 monitors upper displacement (e.g., the combined displacement of the bolt flange 124, the bolt head 125, the plate 140 and the washer 150) and the sensor 71 monitors total displacement (e.g., the upper displacement seen by sensor 61 and displacement caused by lower bolt portions). At the same time, the camera 62 visually records changes in the upper-displacement components, the camera 72 visually records changes in the bolt body 121, and the microphone 63 audibly records relevant sounds. This data is conveyed to the collection station 80 and to the output station 90, for compilation into an easily understandable format.

As shown in FIGS. 8A-8H, test data can be output in video formats, graphical formats, and/or audio formats. The combination of some or all of these formats may often provide the meaningful analysis. For example, visual images corresponding to plotted points correlate component deformation with force curves to fully appreciate failure sequences during testing.

The invention claimed is:

1. An apparatus (10) for tensile testing of a tendon-type support system (100), said apparatus (10) comprising:
    a force-imposing device (20) for imposing force on the support system (100) in a direction and in a manner corresponding to the force imposed in its expected installation condition;
    a platen (40) for posing the support system (100) in a manner mimicking its expected installation condition;
    a position sensor (61) for sensing position changes of certain components in the force-imposing direction;
    another position sensor (71) for sensing position changes of the entire support system (100);
    a data collection station (80) for collecting data relating to the force imposed by the force-imposing device (20) and data relating to position changes sensed by the position sensors (61,71) at such force; and
    an output station (90) for outputting the collected data in a format allowing analysis of the system (100) in its entirety.

2. An apparatus (10) as set forth in claim 1, wherein the output station (90) outputs the collected data in a graphical form with a plot showing the correlation between the force imposed by the device (20) and position changes sensed by the sensor (61) and/or the sensor (71).

3. An apparatus (10) as set forth in claim 1, wherein the plot depicts the displacement sensed by position sensor (61), the displacement sensed by position sensor (71), and the difference therebetween.

4. An apparatus (10) as set forth in claim 1, comprising a camera (62) for visually recording images showing regions of the support system (100) near the position sensor (61) and/or a camera (72) for visually recording images showing regions of the support system (100) near the position sensor (71), and wherein the output station (90) correlates these images to the forces imposed by the device (20) and/or the position changes sensed by the sensors (61, 71).

5. An apparatus (10) as set forth in claim 4, comprising a microphone (63) for audibly recording sounds associated with the support system (100) and wherein the output station (90) correlates these sounds to the forces imposed by the device (20) and/or the position changes sensed by the sensors (61, 71).

6. An apparatus (10) as set forth in claim 1, wherein the force-imposing device (20) comprise a cylinder (21) having central bore (22) and annular fluid chamber (23) therearound, and a ram (24) slidably mounted within the fluid chamber (23) so as to be urged vertically in response to fluid contained therein.

7. An apparatus (10) as set forth in claim 6, wherein the ram (24) has central bore (25) aligned with the central bore (22) of the cylinder (21).

8. An apparatus (10) as set forth in claim 6, wherein the force-imposing device (20) is mounted on a table having a horizontal platform (31) and wherein the cylinder (21) extends at least partially through an opening (33) in the platform (31) and is held in place by a bracket (34).

9. An apparatus (10) as set forth in claim 6, wherein the platen (40) is fixed to the top of the cylinder (21) and has central bore (41) aligned with the central bore (22) of the cylinder (21).

10. An apparatus (10) as set forth in claim 9, wherein the platen (40) has an upper surface (42) surrounding its central bore (41) and including a counterbore (43).

11. An apparatus (10) as set forth in claim 6, further comprising coupling contraptions (50) for coupling the to-be-tested support system to the force-imposing device (20).

12. An apparatus (10) as set forth in claim 11, wherein the fixturing assembly (50) includes a pipe (51) having a central bore (54) alignable with the central bore (25) of the ram (24), wherein the pipe (51) moves with the ram (24).

13. An apparatus (10) as set forth in claim 12, wherein the fixturing assembly (50) includes a washer (52) having central opening 55 alignable with the pipe's central bore (54) and the ram's central bore (25).

14. An apparatus (10) as set forth in claim 12, wherein the fixturing assembly (50) includes wedge locking elements (53).

15. An apparatus (10) as set forth in claim 1, wherein the output station (90) is contained within a laptop computer.

16. An apparatus (10) as set forth in claim 1, wherein a camera (62) visually records images showing regions of the support system (100) near the position sensor (61) and a camera (72) visually records images showing regions of the support system (100) near the position sensor (71);
    wherein the output station (90) outputs the collected data in a graphical form with a plot showing the correlation between the forces imposed by the device (20) and the position changes sensed by the sensor (61) and a plot showing the correlation between forces imposed by the device (20) and the position changes sensed by the sensor (71); and
    wherein the output station (90) correlates these images to the forces imposed by the device (20) and/or the position changes sensed by the sensors (61, 71).

17. An apparatus (10) as set forth in claim 1, wherein the force-imposing device (20) comprises a cylinder (21) and a ram (24) which moves downward when fluid is supplied to the cylinder (21); wherein the platen (40) is fixed to the cylinder (21); and wherein the cylinder (21), the ram (24), and the platen (40) include aligned central bores adapted to receive a cylindrical bolt body (121) of the tendon-type support system (100).

18. An apparatus (10) as set forth in claim 16, wherein the position sensor (61) is located above the platen (40) and wherein a camera (62) visually records images showing regions of the support system (100) mounted on the platen (40); and wherein the position sensor (71) is located below the ram (24) and wherein a camera (72) visually records images showing regions of the support system (100) below the ram (24);

wherein the output station (90) correlates the images recorded by the cameras (62, 72) to the forces imposed by the device (20) and/or the position changes sensed by the sensors (61, 71).

19. A method of tensile testing of a tendon-type support system (100) with the apparatus (10) set forth in claim 1, said method comprising:

installing the support system (100) on the platen (40), activating the force-imposing device (20) to impose force on the platen-installed support system (100);

collecting data at the station (80) relating to the force imposed by the force-imposing device (20) and data relating to position changes sensed by the position sensors (61, 71) at such forces; and outputting the collected data at the station (90) in a format allowing analysis of the support system (100).

20. An apparatus (10) for tensile testing of a tendon-type support system (100) having a bolt body (121) which is anchored to a borehole (101) in an expected installation condition, said apparatus (10) comprising:

a platen (40) for situating the support system (100) in a manner mimicking its expected installation condition;

a force-imposing device (20) for imposing force on the support system (100) in a direction and in a manner corresponding to the force imposed in its expected installation condition; and a position sensor (61, 71) for sensing position changes of certain components and/or the system (100) in the force-imposing direction.

* * * * *